(12) United States Patent
Johansson et al.

(10) Patent No.: US 7,385,040 B2
(45) Date of Patent: Jun. 10, 2008

(54) ANTIBODY PURIFICATION

(75) Inventors: Bo-Lennart Johansson, Uppsala (SE);
Hans J. Johansson, Uppsala (SE);
Anders Ljunglöf, Uppsala (SE);
Jean-Luc Maloisel, Uppsala (SE);
Nicolas Thevenin, Uppsala (SE)

(73) Assignee: GE Healthcare Bio-Sciences AB, Uppsala (SE)

(*) Notice: Subject to any disclaimer, the term of this patent is extended or adjusted under 35 U.S.C. 154(b) by 28 days.

(21) Appl. No.: 10/589,718

(22) PCT Filed: Feb. 24, 2005

(86) PCT No.: PCT/SE2005/000292

§ 371 (c)(1),
(2), (4) Date: Aug. 16, 2006

(87) PCT Pub. No.: WO2005/082926

PCT Pub. Date: Sep. 9, 2005

(65) Prior Publication Data

US 2007/0112178 A1     May 17, 2007

(30) Foreign Application Priority Data

Feb. 27, 2004  (SE) .................................. 0400501

(51) Int. Cl.
*C07K 1/18*     (2006.01)
*C07K 1/22*     (2006.01)

(52) U.S. Cl. ............. 530/413; 210/660; 210/691; 210/692; 436/547; 436/548; 530/390.5; 530/415; 530/416

(58) Field of Classification Search .............. None
See application file for complete search history.

(56) References Cited

U.S. PATENT DOCUMENTS

| | | | |
|---|---|---|---|
| 4,983,722 A | 1/1991 | Bloom et al. | |
| 5,151,350 A | 9/1992 | Colbert et al. | |
| 5,429,746 A | 7/1995 | Shadle et al. | |
| 6,117,996 A * | 9/2000 | Lowe et al. | 544/216 |
| 6,498,236 B1 | 12/2002 | Lihme et al. | |
| 6,852,230 B2 * | 2/2005 | Belew et al. | 210/635 |
| 2002/0110495 A1* | 8/2002 | Hunt et al. | 422/101 |
| 2003/0153735 A1 | 8/2003 | Breece et al. | |

FOREIGN PATENT DOCUMENTS

| | | |
|---|---|---|
| EP | 0 345 549 | 4/1995 |
| WO | WO 84/00773 | 3/1984 |
| WO | WO 97/10887 | 3/1997 |
| WO | WO 02/05959 | 1/2002 |
| WO | WO 02/053288 * | 7/2002 |
| WO | WO 03/024588 | 3/2003 |
| WO | WO 03/041859 | 5/2003 |
| WO | WO 2004/076485 | 9/2004 |

OTHER PUBLICATIONS

Johansson, B., et al., "Preparation and Characterization of Prototypes for Multi-Modal Separation Aimed for Capture of Positively Charged Biomolecules at High-Salt Conditions", *Journal of Chromatography A*, vol. 1016, 2003, p. 34-49.

Kastner, M., "Protein Liquid Chromatography", *Journal of Chromatography Library*, vol. 61, 2000, p. 61.

* cited by examiner

*Primary Examiner*—David A Saunders
(74) *Attorney, Agent, or Firm*—Yonggang Ji

(57) ABSTRACT

The present invention relates to a method of separating antibodies from contaminants in a solution, which method comprises contacting the solution with a chromatography resin comprised of a support to which multi-modal ligands have been immobilised, wherein a multi-modal ligand comprises at least one cation-exchanging group and at least one aromatic or heteroaromatic ring system. In one embodiment, the ring-forming atoms of the aromatic or hereoaromatic entity are selected among C, S or O, and the cation exchanging group is a weak cation exchanger. The present method may be used as a single step procedure or as a polishing step following a capture on a Protein A column.

8 Claims, 14 Drawing Sheets

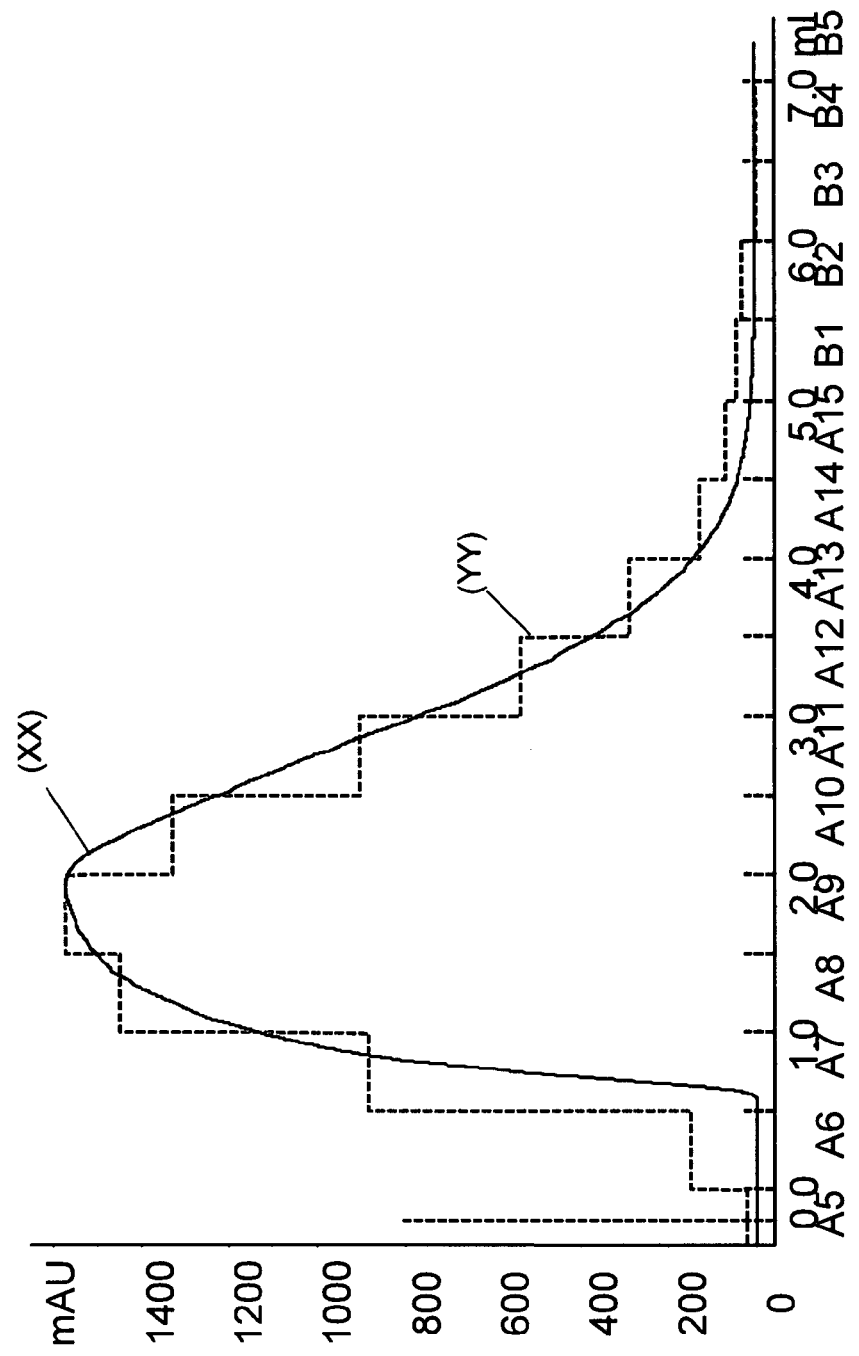
Figure 1  Control Experiment 1

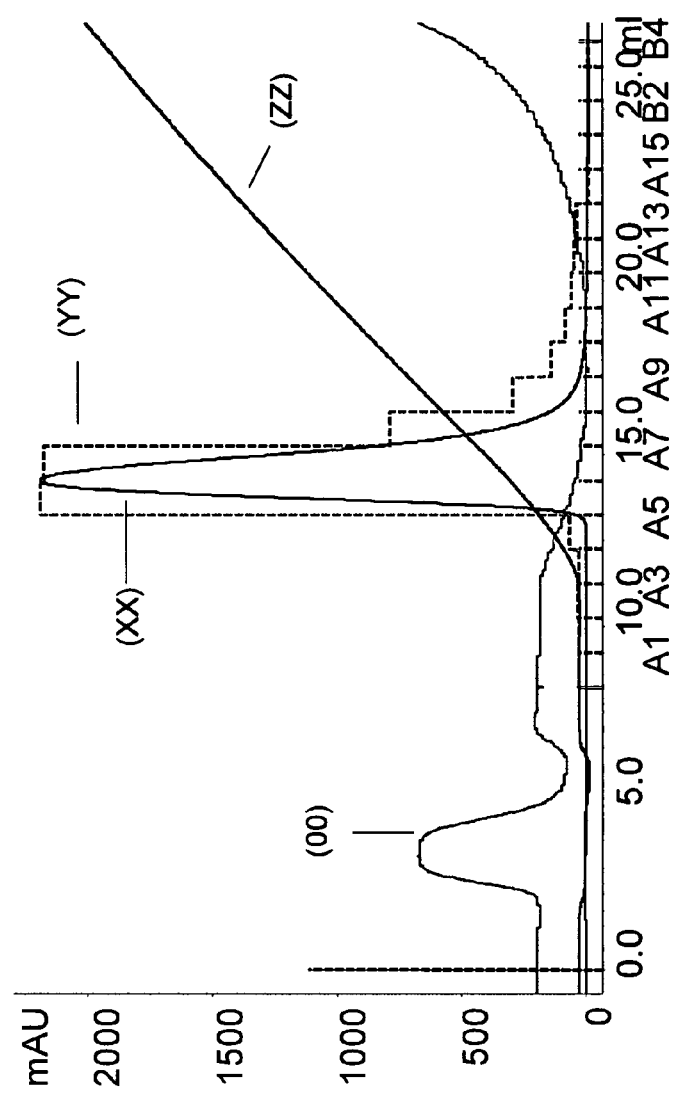
Figure 2  Control Experiment 2

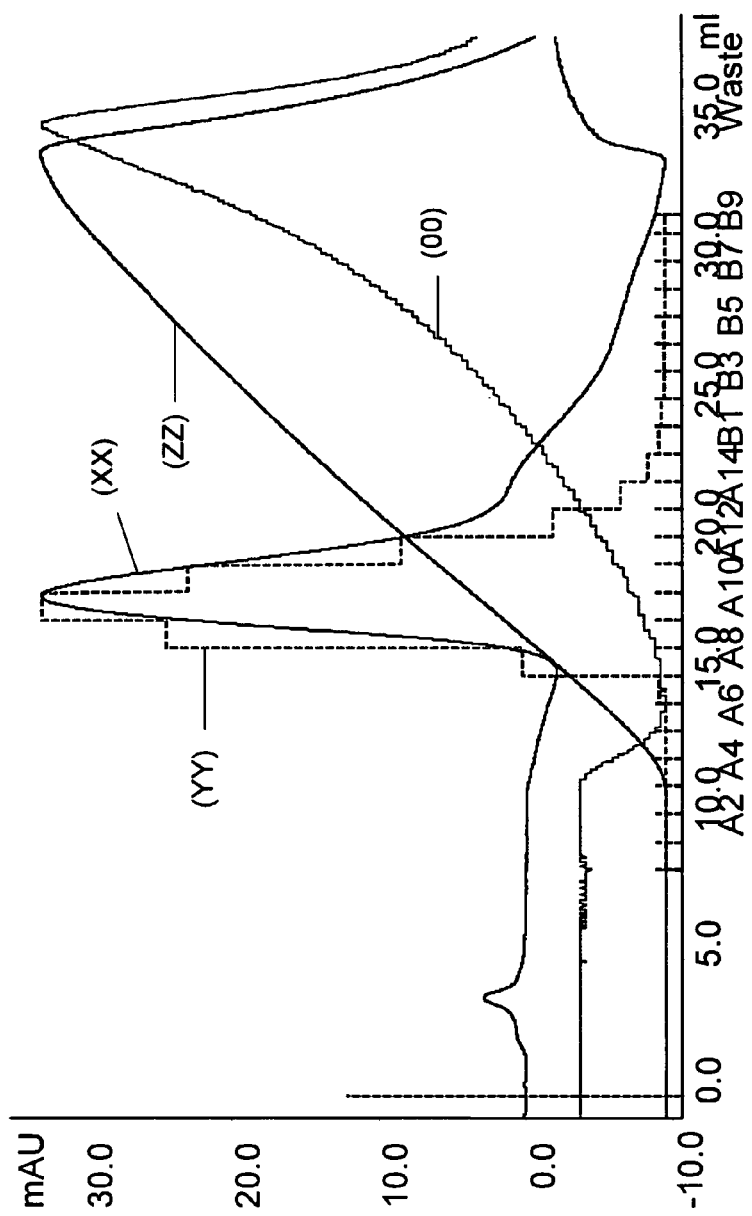
Figure 3  Control Experiment 3

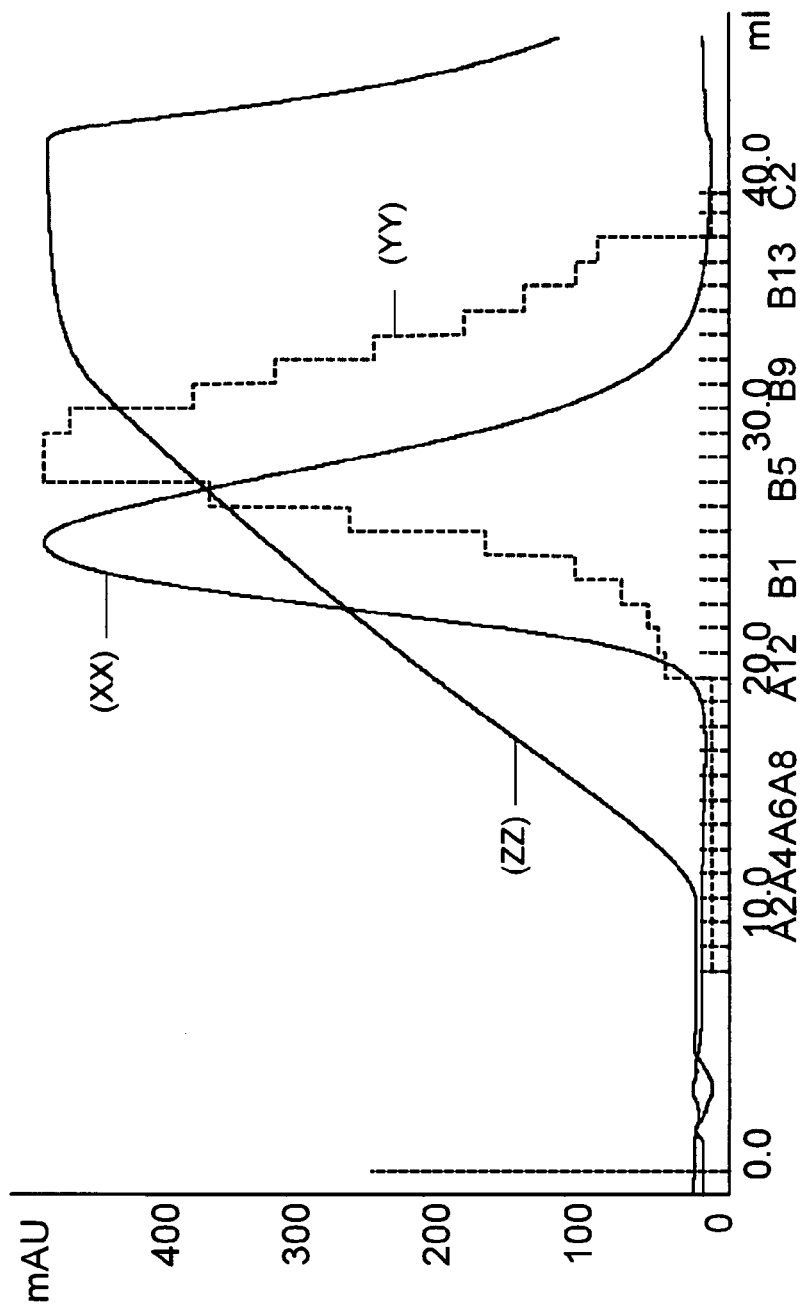
Figure 4 Separation in Binding Mode

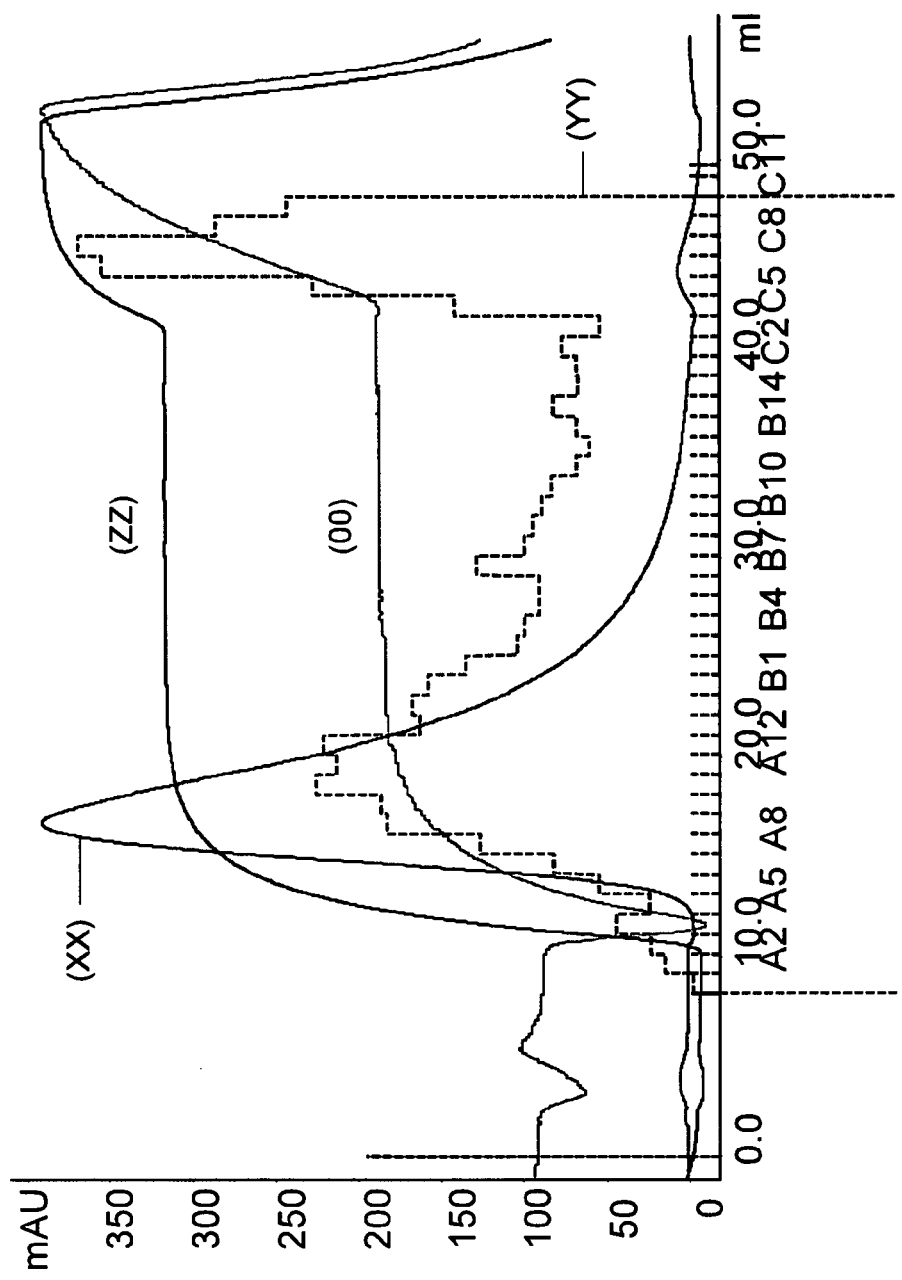
Figure 5  Separation in Optimised Binding Mode

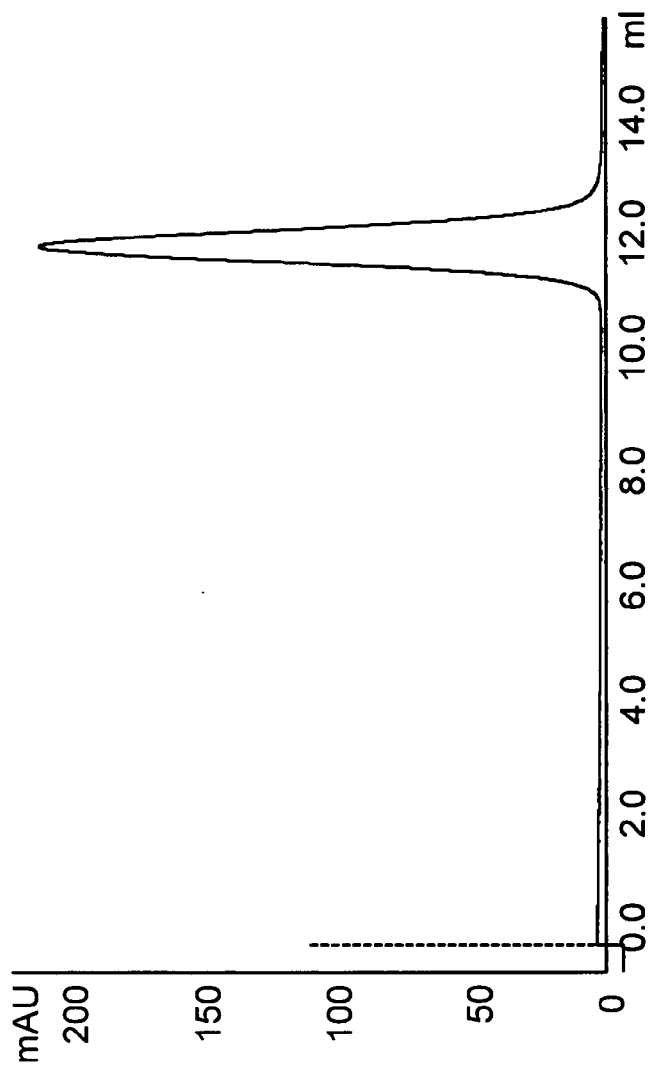
Figure 6A Gel Filtration of Peaks from Figure 5 – Fraction A9

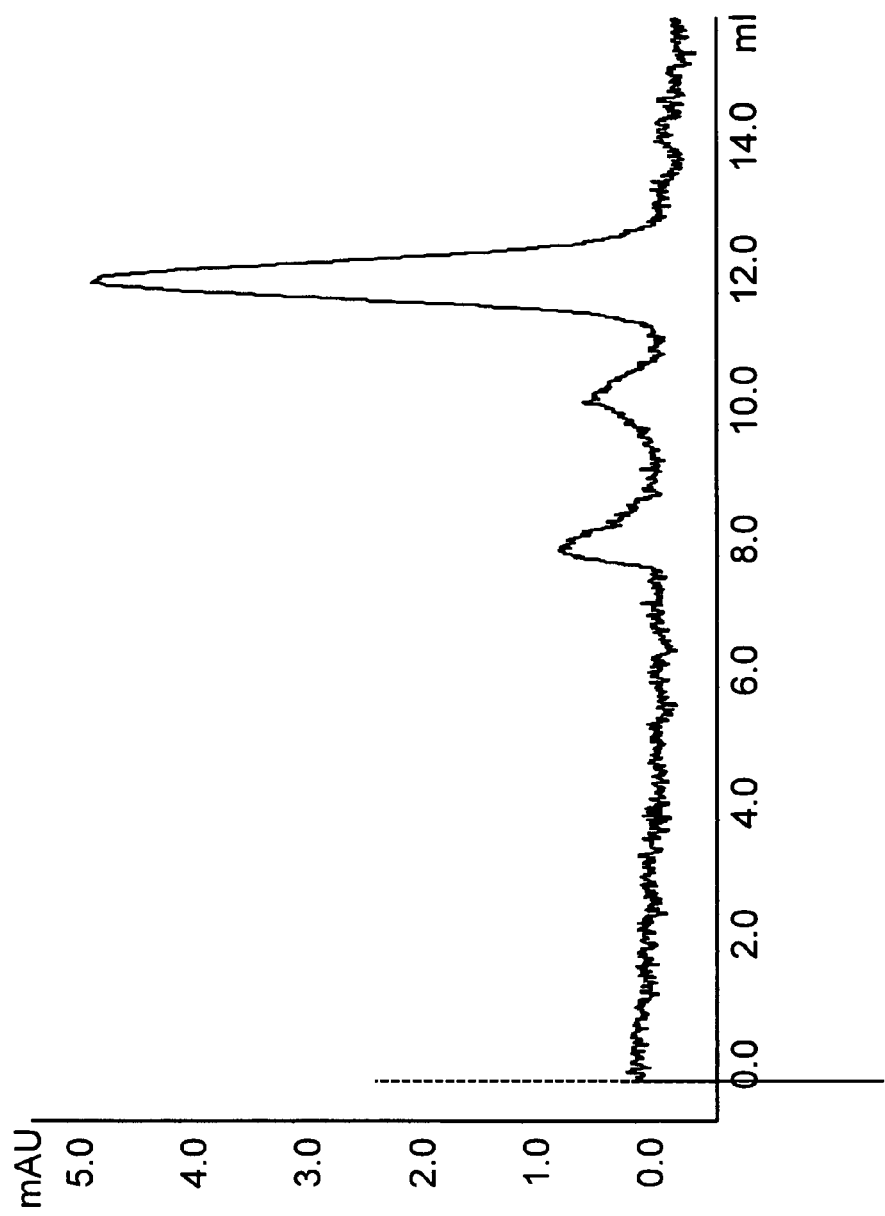
Figure 6B Gel Filtration of Peaks from Figure 5 – Fraction C7

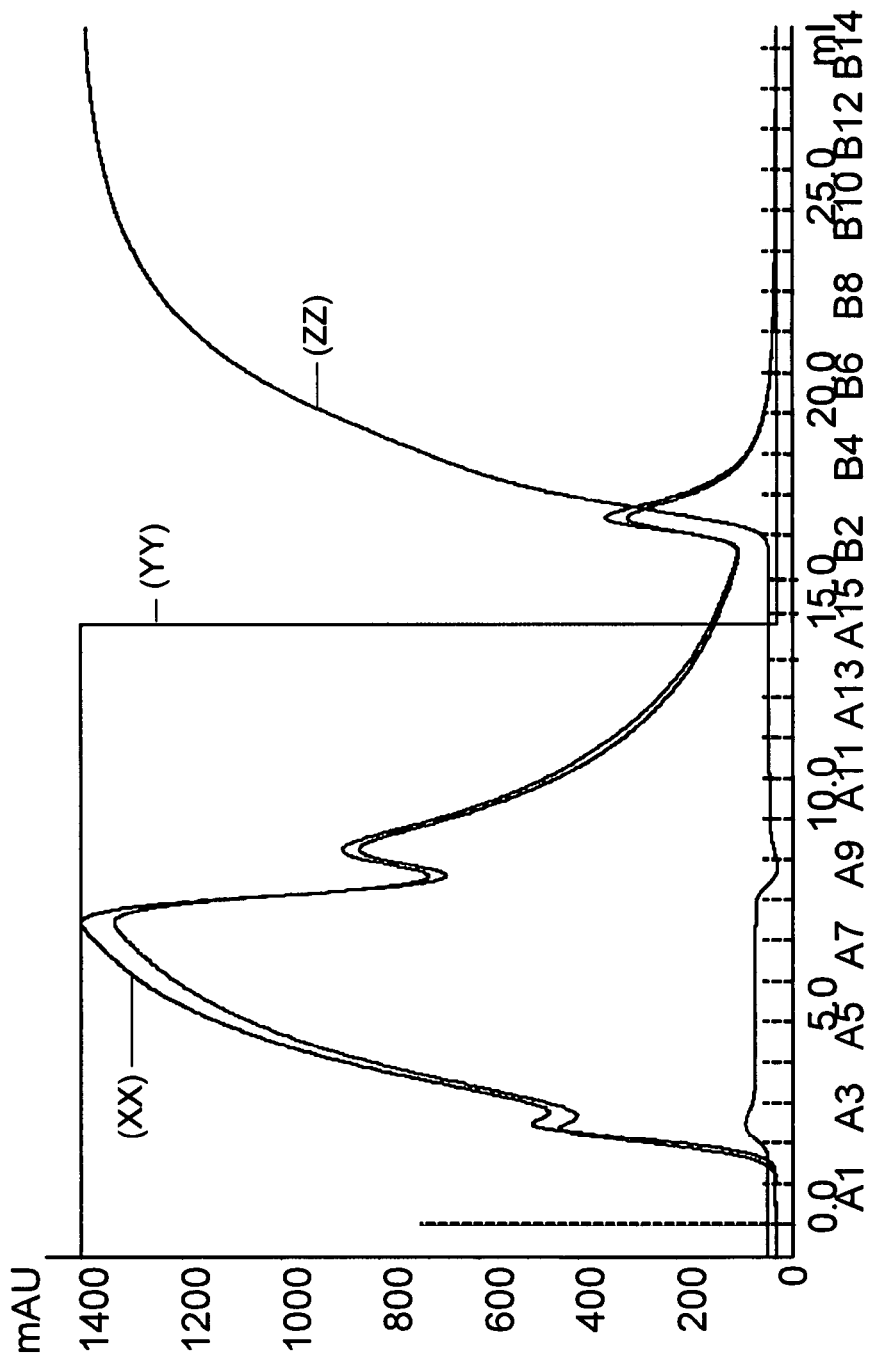
Figure 7 Separation in Flow Through Mode

Figure 8A Gel Filtration of Peaks from Figure 7
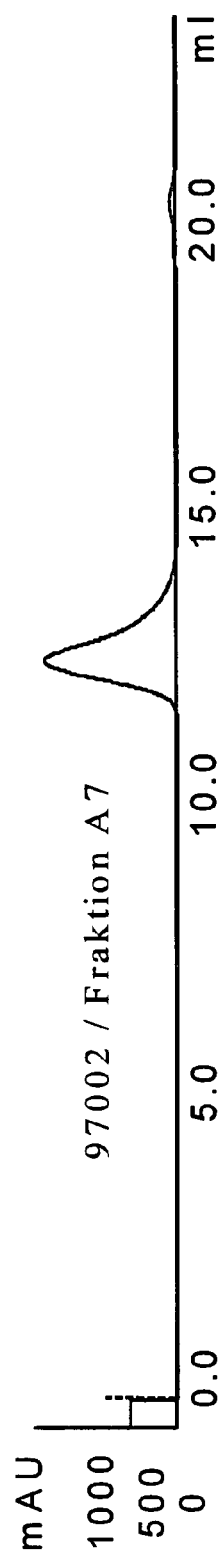

Figure 8B Gel Filtration of Peaks from Figure 7
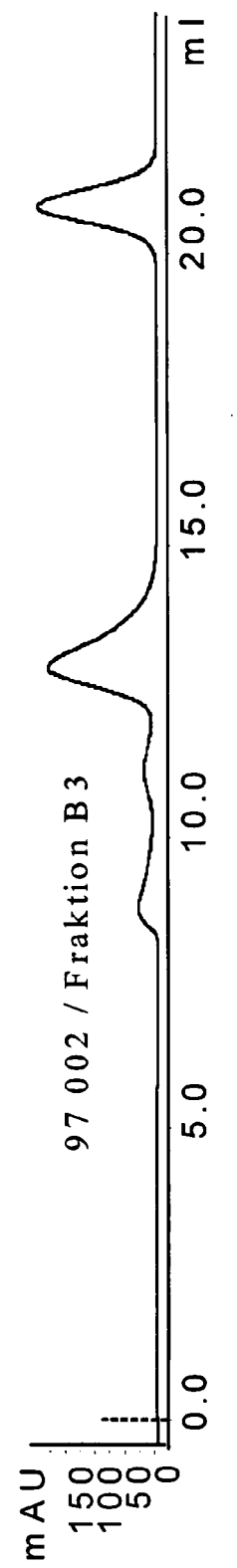

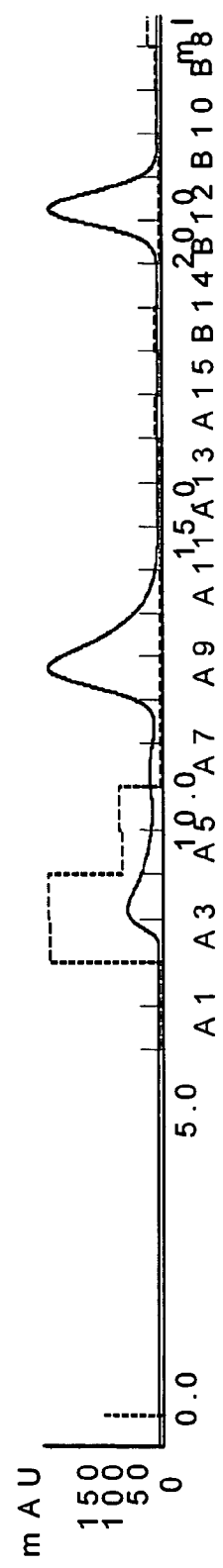
Figure 8C Gel Filtration of Peaks from Figure 7

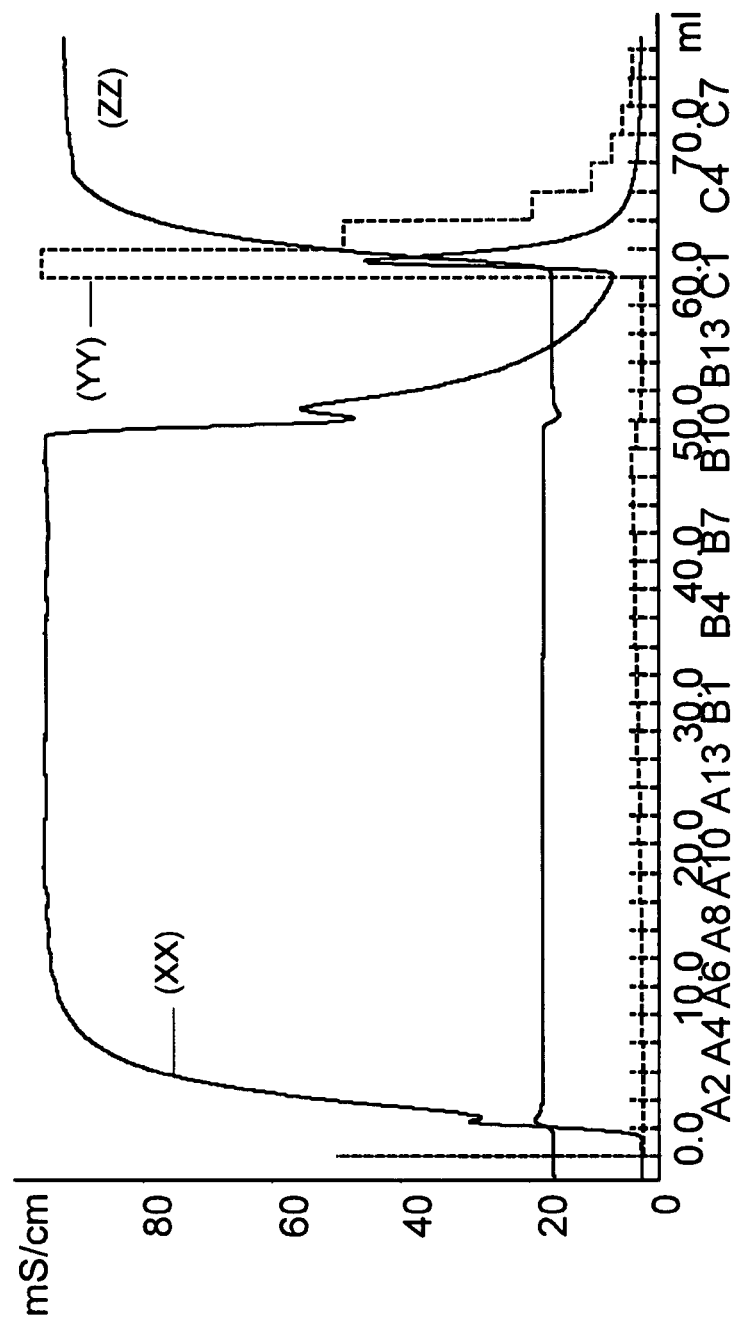
Figure 9 Separation in Flow Through Mode

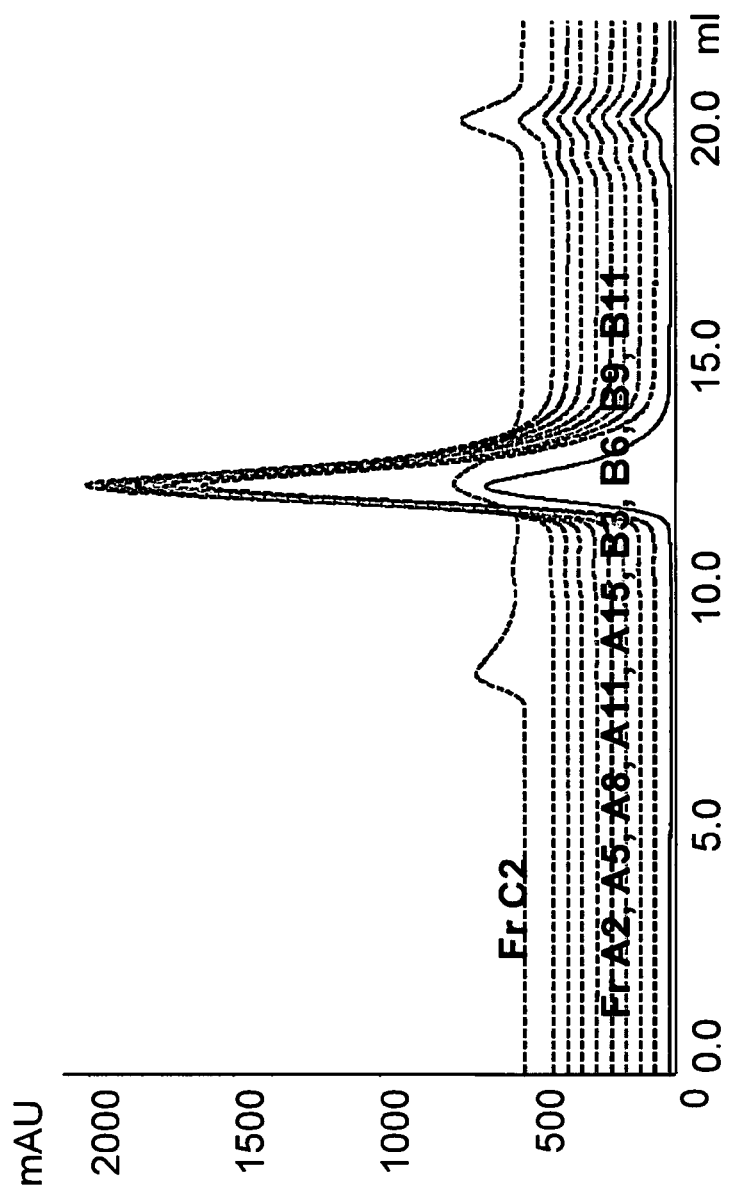
Figure 10A Gel Filtration of Peaks from Figure 9

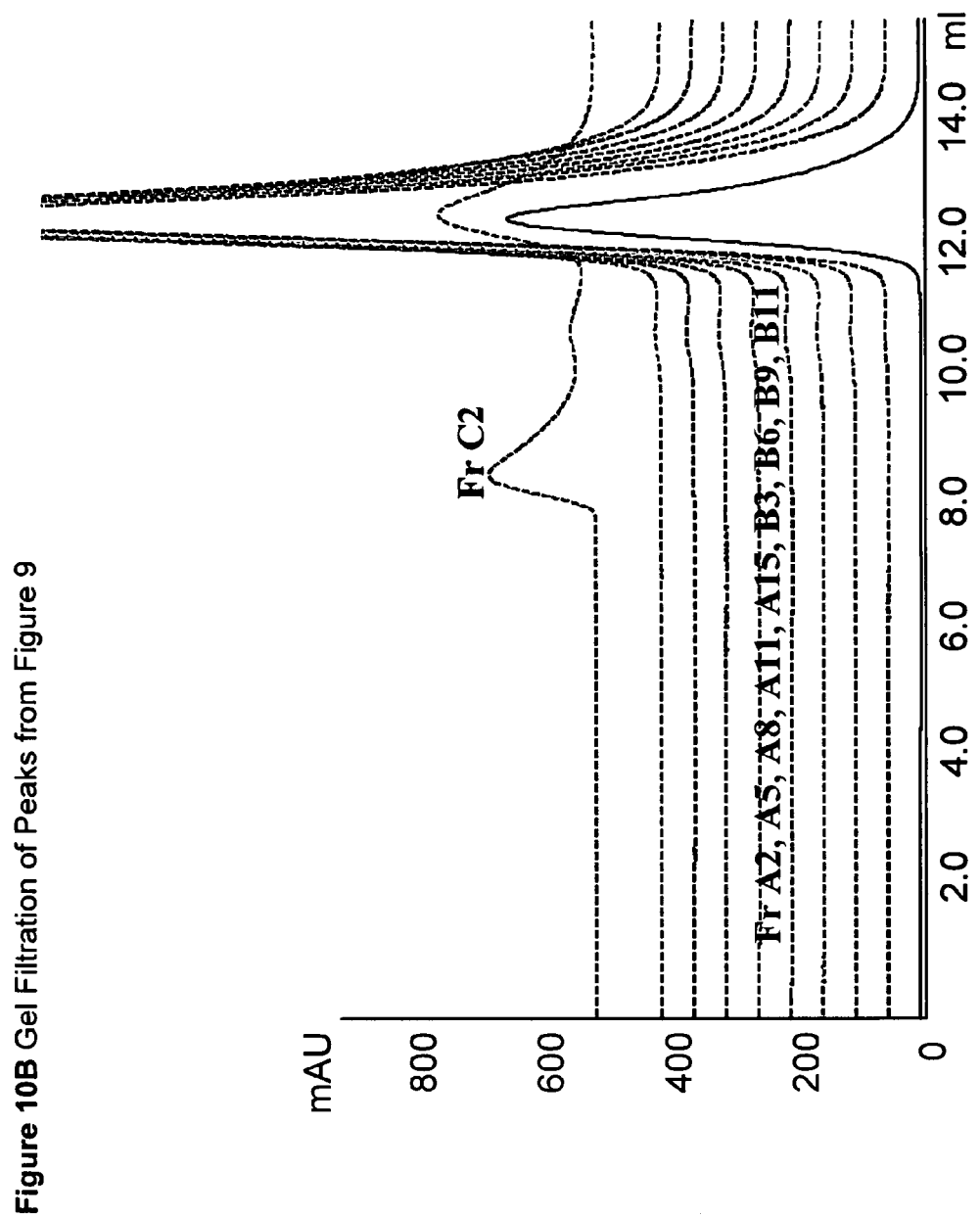
Figure 10B Gel Filtration of Peaks from Figure 9

ANTIBODY PURIFICATION

CROSS REFERENCE TO RELATED APPLICATIONS

This application is a filing under 35 U.S.C. 371 and claims priority to international patent application number PCT/SE2005/000292 filed Feb. 24, 2005, published on Sep. 9, 2005, as WO 2005/082926, which claims priority to application number 0400501-3 filed in Sweden on Feb. 27, 2004.

TECHNICAL FIELD

The present invention relates to a method of purification of antibodies. More specifically, the present method is advantageously used as a step subsequent to affinity chromatography to remove contaminants that result from the affinity resin. The present invention also encompasses a kit for purification of antibodies from contaminating complexes formed between antibodies and residues from an affinity chromatography resin.

BACKGROUND

The immune system is composed of many interdependent cell types that collectively protect the body from bacterial, parasitic, fungal, viral infections and from the growth of tumour cells. The guards of the immune system are macrophages that continually roam the bloodstream of their host. When challenged by infection or immunisation, macrophages respond by engulfing invaders marked with foreign molecules known as antigens. This event, mediated by helper T cells, sets forth a complicated chain of responses that result in the stimulation of B-cells. These B-cells, in turn, produce proteins called antibodies, which bind to the foreign invader. The binding event between antibody and antigen marks the foreign invader for destruction via phagocytosis or activation of the complement system. A number of different classes of antibodies, or immunoglobulins, exist, such as IgA, IgD, IgE, IgG, and IgM. They differ not only in their physiological roles but also in their structures. From a structural point of view, IgG antibodies are a particular class of immunoglobulins that have been extensively studied, perhaps because of the dominant role they play in a mature immune response.

The biological activity, which the immunoglobulins possess, is today exploited in a range of different applications in the human and veterinary diagnostic, health care and therapeutic sector. In fact, in the last few years, monoclonal antibodies and recombinant antibody constructs have become the largest class of proteins currently investigated in clinical trials and receiving FDA approval as therapeutics and diagnostics. Complementary to expression systems and production strategies, purification protocols are designed to obtain highly pure antibodies in a simple and cost-efficient manner.

Traditional methods for isolation of immunoglobulins are based on selective reversible precipitation of the protein fraction comprising the immunoglobulins while leaving other groups of proteins in solution. Typical precipitation agents are ethanol, polyethylene glycol, lyotropic salts such as ammonium sulphate and potassium phosphate, and caprylic acid. Typically, these precipitation methods are giving very impure products while at the same time being time consuming and laborious. Furthermore, the addition of the precipitating agent to the raw material makes it difficult to use the supernatant for other purposes and creates a disposal problem, which is particularly relevant when speaking of large-scale purification of immunoglobulins.

An alternative method for isolation of immunoglobulins is chromatography, which embraces a family of closely related separation methods. The feature distinguishing chromatography from most other physical and chemical methods of separation is that two mutually immiscible phases are brought into contact wherein one phase is stationary and the other mobile. The sample mixture, introduced into the mobile phase, undergoes a series of interactions many times before the stationary and mobile phases as it is being carried through the system by the mobile phase. Interactions exploit differences in the physical or chemical properties of the components in the sample. These differences govern the rate of migration of the individual components under the influence of a mobile phase moving through a column containing the stationary phase. Separated components emerge in the order of increasing interaction with the stationary phase. The least retarded component elutes first, the most strongly retained material elutes last. Separation is obtained when one component is retarded sufficiently to prevent overlap with the zone of an adjacent solute as sample components elute from the column. Efforts are continuously being made to design the optimal stationary phase for each specific separation purpose. Such a stationary phase is commonly comprised of a support or base matrix to which a ligand comprising functional i.e. binding groups has been attached. Reference is commonly made to each kind of chromatography based on the principle of interaction utilised.

Thus, ion exchange chromatography is frequently used for isolation of immunoglobulins. In anion exchange chromatography, negatively charged amino acid side chains of the immunoglobulin will interact with positively charged ligands of a chromatography matrix. In cation exchange chromatography on the other hand, positively charged amino acid side chains of the immunoglobulin will interact with negatively charged ligands of a chromatography matrix.

Hydrophobic interaction chromatography (HIC) is also a method widely described for isolation of immunoglobulins. However, hydrophobic matrices require an addition of lyotropic salts to the raw material to make the immunoglobulin bind efficiently. The bound antibody is released from the matrix by lowering the concentration of lyotropic salt in a continuous or stepwise gradient. If a highly pure product is the object, it is recommended to combine the hydrophobic chromatography with a further step. Thus, a disadvantage of this procedure is the necessity to add lyotropic salt to the raw material as this gives problems and thereby increased cost to the large-scale user. For other raw materials than cell culture supernatants such as whey, plasma, and egg yolk the addition of lyotropic salts to the raw materials would in many instances be prohibitive in large-scale applications as the salt could prevent any economically feasible use of the immunoglobulin depleted raw material. An additional problem in large-scale applications would be the disposal of several thousand litres of waste.

Protein A and Protein G affinity chromatography are popular and widespread methods for isolation and purification of immunoglobulins, particularly for isolation of monoclonal antibodies, mainly due to the ease of use and the high purity obtained. Used in combination with ion exchange, hydrophobic interaction, hydroxyapatite and/or gel filtration steps, especially protein A-based methods have become the antibody purification method of choice for many biopharmaceutical companies, see e.g. WO 8400773 and U.S. Pat. No. 5,151,350. However, despite their common usage and many advantages, it is well known protein A-based chromatography resins due to the peptidic bonds of the ligands present a certain degree of alkaline sensitivity. In addition, when Protein A-based resins are used to purify antibodies from cell culture media, the presence of proteases therein may result in leakage of Protein A ligands or peptidic fragments thereof. Since most of the leaked Protein A will still tend to form complexes with antibody, the eluent from an affinity column may consequently comprise antibody contaminated with Protein A-antibody complexes as well as Protein A.

An attempt to reduce ligand leakage from affinity chromatography matrices has been presented in WO 03/041859 (Boehringer Ingelheim Pharma KG), wherein it is suggested to pretreat e.g. Protein A matrices with at least one surfactant to reduce ligand leakage. The affinity matrix may be treated e.g. with 5-15 bed volumes of surfactant. The contact time is crucial for the effectiveness of the process. For example, at room temperature, a contact time of at least 16 h is required for a reduction in leakage. At higher temperatures, the contact time may be shorter.

An alternative approach to the problem of ligand leakage is provided in U.S. Pat. No. 4,983,722 (Miles Inc.), wherein Protein A is selectively isolated from an antibody-Protein A mixture by exposing the mixture to an anion exchange material to adsorb both components and then sequentially eluting the antibodies and Protein A under conditions of increasing ionic strength. An illustrative anion exchanger is diethylaminoethyl (DEAE) Trisacryl M or DEAE Sepharose™.

U.S. Pat. No. 5,429,746 (SmithKline Beecham Corp.) relates to the application of hydrophobic interaction chromatography as one step in the purification of antibodies. It is disclosed that HIC can be used following affinity chromatography employing e.g. Protein A, optionally with an intermediate cation exchange chromatography step. The cation exchange chromatography is illustrated by a weak cation exchanger (CM Sepharose™ FF), which is adjusted to pH 5.5 for adsorption and eluted with an elution buffer of 40 mM citrate, 100 mM sodium chloride, pH 6. The mixture applied to the HIC column, following affinity and/or cation exchange chromatography, may then contain contaminants such as immunoglobulin aggregates, misfolded species, host cell protein and residue material from the affinity chromatography step. In such a process, antibody is first adsorbed to a Protein A chromatographic support and eluted; then adsorbed to the cation exchange chromatographic support and selectively eluted there from; and finally adsorbed to a HIC support and eluted.

Ceramic hydroxyapatite has also been suggested as useful for immunoglobulin polishing. More specifically, it has been reported (Chromatography, tech note 2849; S. G. Franklin, Bio-Rad Laboratories, Inc., 2000 Alfred Nobel Drive, Hercules, Calif. 94547 USA) that IgG1 can be resolved from an IgG1-Protein A complex in unfractionated media on CHT ceramic hydroxyapatite (Bio-Rad). More specifically, hydroxyapatite $(Ca_{10}(PO_4)_6(OH)_2)$ is a form of calcium phosphate, which has been shown to possess unique separation properties. However, hydroxyapatite-based matrices are also known to involve certain disadvantages. For example, due to Ca-leakage, they are unstable at acidic pH values, and they are sensitive to chelating agents such as EDTA. In addition, it has been shown that it is difficult to develop, and to scale up, a robust and reproducible purification method using hydroxyapatite-based matrices, e.g. because it has been difficult to pack hydroxyapatite, and to maintain the performance, in large columns. Finally, there is a risk of alterations of the resin properties caused by metal ion contamination and exchange of calcium ions, which alterations is a serious concern for regulatory authorities.

In order to avoid the stability problems and leakage from protein-based affinity columns, purely chemical resins with different selectivities have been suggested. For example, multi-modal chromatography, wherein two or more different, but co-operative, sites interact with a target, has been suggested for antibody purification. More specifically, MBI Hypercel® (BioSepra), an adsorbent comprising mercapto-benzimidazole-sulphonic acid ligands, is stated to provide hydrophobic as well as ionic interactions with monoclonal and polyclonal antibodies. The hydrophobic interactions are assumed to be due to the aromatic ring system, while the ionic interactions should be due to the $SO_3^-$ substituent, which is known as a strong cation exchanger. In addition, the nitrogen atoms of the aromatic system of the MBI ligand are chargeable under certain conditions, and can consequently provide ionic interactions with negatively charged groups. MBI Hypercel® has been disclosed as an alternative to protein A-based resins for the capture and purification of therapeutic and diagnostic antibodies.

U.S. Pat. No. 6,498,236 (Upfront Chromatography) discloses a method for the isolation or purification of immunoglobulins from a solution, such as a hybridoma cell culture supernatant, animal plasma or sera. The method is suggested as an alternative to the use of Protein A, Protein G, synthetic peptides and other relatively high molecular weight ligands, which are stated to involve drawbacks due to the small difference between the respective molecular weights of the ligands and the immunoglobulins, as well as to their natural tendency to bind to each other. According to U.S. Pat. No. 6,498,236, it is decisive which substituents are present on a ligand, such as a benzene ring, as to whether the ligand will be binding the immunoglobulins efficiently. More specifically, the solid phase matrices used in the disclosed method are described by the formula M-SP1-X-A-SP2-ACID, wherein M designates the matrix backbone, SP1 designates a spacer, X designates O, S or NH, A designates a mono- or bicyclic optionally substituted aromatic or heteroaromatic moiety, SP2 designates an optional spacer and ACID designates an acidic group. The ligand is preferably derived from compounds selected from the group consisting of benzimidazoles, benzothiazoles, and benzoxazoles.

WO 97/10887 (Novo Nordisk A/S) relates to conjugates of affinity ligand-matrix useful in the purification of proteinaceous materials such as immunoglobulins, insulins, Factor VII or human growth hormone or analogues, derivatives and fragments thereof. The WO 97/10887 invention is based on the notion that the selectivity of hydrophobic ligands may be increased by increasing the complexity and spatial geometry of the hydrophobic component. This notion led to the discovery of a generic group of affinity ligands, which group is limited to structures having a heteroaromatic entity wherein at least one ring-forming atom is nitrogen. The ligands disclosed in WO 97/10887, which were designed by computer modelling techniques and/or screening of mimetic ligand libraries, are suggested for use in place of Protein A or Protein G, which are both well known ligands for capture of immunoglobulins from fermentation liquid.

Further, a method of synthesising multi-modal cationic exchanger media is disclosed in WO 03/024588 (Amersham Biosciences AB). More specifically, a scaffold comprising two functionalities, preferably homocysteine thiolactone, is derivatised and reacted with a solid base matrix. More specifically, one of the two functionalities, preferably sulphur, is used for the coupling to the matrix and the second functionality is one that can be transformed into an ionic group. Thus, the multi-modal media so produced will be capable of ionic interaction as well as a further kind of interaction, such as hydrophobic interaction, depending on the nature of the derivatisation. In the experimental part, the produced cation exchangers are tested using three model proteins, namely Cytochrome C (Cyt C), bovine serum albumin (BSA) and immunoglobulin G (IgG).

BRIEF DESCRIPTION OF THE PRESENT INVENTION

In one aspect, the present invention provides a robust method for the purification of antibodies. In a specific aspect of the invention a method is provided for the removing of leakage from an eluate from an affinity chromatography column, such as a Protein A column. This can be achieved as defined in the appended claims.

Thus, in a specific aspect the invention provides a method useful as a supplement to protein A-based affinity chromatography for the purification of monoclonal or polyclonal antibodies of high purity.

In a further aspect the invention provides such a method, which provides different selectivities from currently used polishing methods.

Other aspects and advantages of the present invention will appear from the detailed disclosure that follows.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the results of control experiment, wherein a MAb-Protein A mixture was run through a capillary instead of the column to ensure that the delay volume was correct, as disclosed in the experimental part below.

FIG. 2 shows the results of a second control experiment, wherein Protein A solution was run on a reference matrix (Sepharose™ FF, Amersham Biosciences), as disclosed in the experimental part below.

FIG. 3 shows the results of a third control experiment, wherein a Protein A solution was applied to a multi-modal resin, as disclosed in the experimental part below.

FIG. 4 shows the separation of MAb and MAb-Protein A aggregates in binding mode, as disclosed in the experimental part below.

FIG. 5 shows the separation of MAb and MAb-Protein A aggregates in binding mode, optimised by using an optimised elution scheme, as disclosed in the experimental part below.

FIG. 6 shows the analysis of peaks from FIG. 5 by gel filtration, as described in the experimental part below.

FIG. 7 shows the separation of pure MAb and MAb-Protein A aggregates in 'flow-through mode', i.e. when the MAbs flow through the column without being adsorbed, as described below.

FIG. 8 shows the analysis of peaks from FIG. 7 by gel filtration, as described in the experimental part below.

FIG. 9 shows the separation of pure MAb and MAb-Protein A aggregates in flow-through mode, but using a substantially larger sample volume than in FIG. 7, as described in the experimental part below.

FIG. 10 shows the results of gel filtration analysis of peaks from FIG. 9, as described in the experimental part below.

DEFINITIONS

The terms "antibody" and "immunoglobulin" are used interchangeably in the present specification.

The term "eluent" is used in its conventional meaning in this field, i.e. a buffer of suitable pH and/or ionic strength to release one or more compounds from a separation matrix.

The term "affinity chromatography" means chromatography based on specific interactions between a target biomolecule and a biospecific ligand in a principle of lock-key recognition. Thus, the target and ligand will constitute an affinity pair, such as antigen/antibody, enzyme/receptor etc.

The term "chromatography resin" is used herein to denote a carrier to which functional groups, known as ligands, have been coupled.

The term "multi-modal chromatography ligand" refers to a ligand that is capable of providing at least two different, but co-operative, sites which interact with the substance to be bound. One of these sites gives an attractive type of charge-charge interaction between the ligand and the substance of interest. The other site typically gives electron acceptor-donor interaction and/or hydrophobic and/or hydrophilic interactions. Electron donor-acceptor interactions include interactions such as hydrogen-bonding, $\pi$-$\pi$, cation-$\pi$, charge transfer, dipole-dipole, induced dipole etc. Multi-modal chromatography ligands are also known as "mixed mode" chromatography ligands.

The phrase "electron donor-acceptor interactions" means that an electronegative atom with a free pair of electrons acts as a donor and bind to an electron-deficient atom that acts as an acceptor for the electron pair of the donor. (See e.g. Karger et al., An Introduction into Separation Science, John Wiley & Sons (1973) page 42.)

The term "cation exchanging group" means herein a group which is negatively charged or chargeable.

The term "capture step" refers in the context of liquid chromatography to the initial step of a separation procedure. Most commonly, a capture step includes clarification, concentration, stabilisation and a significant purification from soluble contaminants. After the capture step, an intermediate purification may follow, which removes most of the significant impurities including DNA, viruses and endotoxins.

The term "polishing step" refers in the context of liquid chromatography to a final purification step, wherein trace contaminants and impurities are removed to leave an active, safe product. Contaminants removed during the polishing step are often conformers of the target molecule or suspected leakage products.

The term an "Fc-binding protein" means a protein capable of binding to the crystallisable part (Fc) of an antibody and includes e.g. Protein A and Protein G, or any fragment or fusion protein thereof that has maintained said binding property.

DETAILED DESCRIPTION OF THE INVENTION

In one aspect, the present invention relates to a method of separating antibodies from one or more contaminants in a solution, which method comprises contacting the solution with a chromatography resin comprised of a support to which multi-modal ligands have been immobilised, wherein a multi-modal ligand comprises at least one cation-exchanging group and at least one aromatic or heteroaromatic ring system, to adsorb antibodies and/or contaminant(s) to the resin.

In an advantageous embodiment, the contaminants are adsorbed to the multimodal ligands, and an essentially pure fraction of antibodies is recovered either as the flow-through, i.e. without being adsorbed, or in the binding mode by a subsequent selective elution. In this context, the term "essentially pure" is understood to mean that substantially all the contaminants have been removed. Most advantageously, at least about 80%, such as at least about 95%, i.e. in the interval of 95-100%, such as at least about 98%, i.e. in the interval of 98-100% and preferably at least about 99%, i.e. in the interval of 99-100%, of the contaminants are removed on the multi-modal chromatography resin. However, as the skilled person in this field will appreciate, the possible purities will depend on the concentration of antibody in the solution applied to the chromatography resin as well as other conditions used.

In a specific embodiment of the present method, the solution applied to the multi-modal chromatography resin is an antibody-containing eluate originating from an affinity chromatography resin. In an advantageous embodiment, the ligands of said affinity chromatography resin comprise an Fc-binding protein, such as Protein A, e.g. native or recombinant protein A. Such affinity resins are commercially available, such as MabSelect™ from Amersham Biosciences. Consequently, in this embodiment, the contaminants to be removed may comprise released Protein A; complexes formed between Protein A and antibodies, such as Protein A-MAb complexes, which complexes may comprise a number of antibodies per Protein A molecule, such as 2-4 antibodies complexed with one Protein A molecule; and aggregates of released Protein A or antibodies.

In an advantageous embodiment, the present method is performed using conventional liquid chromatography, i.e. by passing a solution over a chromatography column. To recover adsorbed substances, elution is performed by passing a buffer over the column. If required, one or more washing steps may be applied before or between any such passage(s). As the skilled person in this field will understand, depending on the specific conditions used in any preceding step, such as affinity chromatography, the resulting eluate may need conditioning by suitable additions or adjustment. It is noted that even though it may be preferred for practical reasons, if an eluate from a Protein A column is to be purified, the present method is not necessarily performed directly following the affinity chromatography, or even in the same facilities.

In one embodiment of the present method solution comprising the desired antibodies is applied to the multi-modal chromatography column in flow-through mode, in which case most of the antibodies will pass directly through while contaminants are adsorbed. The skilled person in this field can easily adapt the conditions to obtain flow-through, e.g. by adjustment of pH, which will depends for example on the charge and charge distribution of the antibodies to be purified. Thus, this embodiment differs essentially from U.S. Pat. No. 6,498,236, wherein the ligands have been specifically selected to bind the immunoglobulins efficiently, as discussed above. In addition, the method disclosed in said U.S. Pat. No. 6,498,236 is not suggested as a supplement to Protein A chromatography, i.e. to remove leakage from a Protein A column, which is one advantageous embodiment of the present invention. A further difference between the present invention and the teachings of U.S. Pat. No. 6,498,236 is the nature of the ligands, as will appear from below.

In an alternative embodiment, the solution comprising the desired antibodies is applied to the multi-modal chromatography column under binding conditions, in which case the antibodies as well as the contaminants are adsorbed to the multi-modal chromatography resin. Again, the skilled person in this field can easily adapt the conditions to obtain the desired binding, e.g. by adjustment of the pH and/or the salt concentration, i.e. the conductivity of the solution.

The multi-modal chromatography resin used in the present method is easily prepared by the skilled person in this field. In brief, the resin is comprised of multi-modal ligands coupled to an organic or inorganic support, sometimes denoted a base matrix, directly or via a spacer. The support may be in the form of particles, such as essentially spherical particles, a monolith, filter, membrane, surface, capillaries, etc. In one embodiment, the support is prepared from a native polymer, such as cross-linked carbohydrate material, such as agarose, agar, cellulose, dextran, chitosan, konjac, carrageenan, gellan, alginate etc. To obtain high adsorption capacities, the support is preferably porous, and ligands are then coupled to the external surfaces as well as to the pore surfaces. Such native polymer supports are easily prepared according to standard methods, such as inverse suspension gelation (S Hjertén: Biochim Biophys Acta 79(2), 393-398 (1964). Alternatively, the support is prepared from a synthetic polymer, such as cross-linked synthetic polymers, e.g. styrene or styrene derivatives, divinylbenzene, acrylamides, acrylate esters, methacrylate esters, vinyl esters, vinyl amides etc. Such synthetic polymers are easily produced according to standard methods, see e.g. "Styrene based polymer supports developed by suspension polymerization" (R Arshady: Chimica e L'Industria 70(9), 70-75 (1988)). Porous native or synthetic polymer supports are also available from commercial sources, such as Amersham Biosciences, Uppsala, Sweden.

A specific example of a support useful for antibody purification with multi-modal ligands is a support for expanded bed adsorption, i.e. a polymer support containing a high density filler, preferably a stainless steel filler. Such an expanded bed adsorption resin is also useful for capture of antibodies, such as monoclonal antibodies, in a capture step.

As mentioned above, the multi-modal ligands of the chromatography resin used in the present method comprises at least one cation-exchanging group and at least one aromatic or heteroaromatic ring system. The aromatic ring system, which is capable of hydrophobic interactions with a target molecule, may comprise of one or two cyclic structures, either separated by one or more atoms or e.g. as a naphtyl group. Further, the ring system is optionally substituted, e.g. with alkyloxy groups, such as methoxy groups. In one embodiment, the aromatic or heteroaromatic ring system does not contain any nitrogen atoms but is limited to carbon atom(s), sulphur atom(s) and oxygen atom(s) as constituting atoms of the cyclic structure. Thus, in an advantageous embodiment, the ring-forming atoms of the aromatic or hereoaromatic entity are selected from the group that consists of C, S and O.

In one embodiment, the resin used in the present method is described as follows: Su-spacer-X-cation exchange group-spacer-aromatic or heteroaromatic ring, wherein Su is a support, the spacers are optional; and X is a coupling atom such as O, S or N. Suitable spacers and coupling chemistries resulting in such spacers are well known in this field. Accordingly, this embodiment differs substantially from the above discussed U.S. Pat. No. 6,498,236, wherein the acidic group that acts as a cation exchange group is a substituent to an aromatic entity. Thus, the resin used in the present embodiment can be expected to allow a different and more spatially extended kind of bond to the target compounds, since the present structure allows a further distance between aromatic and cationic functions. Without wishing to be bound to any theory, it may be hypothesised that the present matrix provides a more favourable adsorption of the relatively large antibody-containing complexes than the U.S. Pat. No. 6,498,236, which is stated to have been optimised for antibody adsorption.

The cation-exchanging group is preferably a weak cation exchanger, i.e. a group which can be protonated at certain pH values. Contrary to weak cation exchangers, strong cation exchange groups comprise groups that maintain charge at all pH values. Thus, in one embodiment, the multi-modal ligands comprise carboxylic groups, such as one or two carboxylic groups.

However, as the skilled person in this field will understand, multi-modal ligands as described above may in addition provide further interactions, such as hydrogen bonding. In addition to the above discussed groups, the multi-modal chromatography ligands used in the present method may also comprise one or more sulphonyl groups, amines or carbonyl groups, which may or may not contribute to the interactions with the contaminants and antibody.

The ligands that are coupled to the above discussed carriers to prepare the multi-modal chromatography resin as used in the present method can e.g. be synthesised as described in the above discussed WO 03/024588 (Amersham Biosciences), wherein multi-modal ligands comprising weak cationic functions are synthesised starting from homocysteine thiolactone. For further references to the synthesis of multi-modal ligands, see e.g. WO 02/059059 (Amersham Biosciences). The ligands may be coupled to the carriers via suitable distancing elements known as spacers. For a review of coupling methods useful to this end, see e.g. Immobilized Affinity Ligand Techniques, Hermanson et al, Greg T. Hermanson, A. Krishna Mallia and Paul K. Smith, Academic Press, INC, 1992. As is well known in this field, parameters such as ligand density or substitution level, pore size of the support etc may be varied to provide a chromatography resin having desired properties.

The present method is useful to recover any monoclonal or polyclonal antibody, such as antibodies originating from mammalian hosts, such as mice, rodents, primates and humans, or antibodies originating from cultured cells such as hybridomas. In one embodiment, the antibodies recovered are human or humanised antibodies. The antibodies may be of any class, i.e. selected from the group that consists of IgA, IgD, IgE, IgG, and IgM. In one embodiment, the antibodies to be purified are antibodies capable of binding to Protein A, or Fc-containing antibody fragments or fusion proteins. In a specific embodiment, the antibodies recovered are immunoglobulin G (IgG). In the present context, it is to be understood that the term "antibodies" also includes antibody fragments and any fusion protein that comprises an antibody or an antibody fragment. Thus, the present invention also encompasses the purification of fragments of any one of the above mentioned antibodies as well as fusion proteins comprising such antibodies. The antibodies isolated according to the present invention are useful as drugs, such as personalised medicine which comprise an active ingredient designed for a specific individual. The antibodies isolated according to the invention are also useful in research and in the diagnostic field.

In one embodiment, the present method comprises a first capture step on a Protein A chromatography resin and a subsequent polishing step on a multi-modal chromatography resin, as described above. The solution applied to the Protein A step may be a cell culture liquid or a fermentation broth, which has optionally been subjected to pretreatment such as filtration, conditioning by adjustment of pH and/or conductivity etc. Thus, the capture step will remove host cell residues such as cell debris and proteins, DNA, endotoxins, and the like, while the polishing step will primarily remove contaminants in the form of residues from the capture step, such as Protein A-antibody aggregates, as discussed above. Accordingly, the present invention provides a more simple procedure than for example the above discussed U.S. Pat. No. 5,429,746 (SmithKline Beecham Corp.), which disclosed two additional steps to follow Protein A-based chromatography. In addition, as compared to the smaller organic ligands suggested as alternatives to Protein A-based chromatography, the present invention allows maintaining the substantial advantages of Protein A as regards selectivity and capacity, while a highly pure antibody product can be obtained.

However, it is understood that purification of antibodies using multi-modal chromatography resins as described herein may well be used as a single step, in which case all of the above exemplified contaminants may be removed. The multi-modal ligands used in such a single step procedure differ from the above discussed multi-modal MBI™ HyperCel ligands in that the atoms that form the aromatic ring system of the present ligands are either limited to carbon atoms, or selected from the group that consists of carbon atoms, sulphur atoms and oxygen atoms, i.e. no nitrogen atoms present in the rings. Since such nitrogens are chargeable, the properties of the MBI™ HyperCel ligands will differ substantially from those of the present ligands under certain conditions. In addition, the present multi-modal ligands comprise only weak cation exchanging groups, contrary to the strong $SO_3^-$ of the MBI™ HyperCel, which is charged at all pH values.

In a second aspect, the present invention is a kit comprising, in separate compartments, a multi-modal chromatography resin; at least two different buffers; and written instructions that describe how to purify antibodies, wherein a multi-modal ligand comprises at least one cation-exchanging group and at least one aromatic or heteroaromatic ring system. In an advantageous embodiment, the instructions gives details for use of the kit to separate antibodies from complexes formed between Protein A and antibodies. In one embodiment, the ring-forming atoms of the aromatic or hereoaromatic entity are selected among C, S or O. The present kit may be used for any one of the above described methods for purification of antibodies. In an advantageous embodiment, the resin is present in a column made from any conventional material, such as a biocompatible plastic, e.g. polypropylene, or glass. The column may be of a size suitable for laboratory scale or large-scale purification of antibodies. In a specific embodiment, the column is provided with luer adaptors, tubing connectors, and domed nuts. In one embodiment, the column is sterile. In a specific embodiment, the column is a disposable.

Finally, another aspect of the invention is a system for purification of antibodies, preferably from cellular components and/or contaminants in a liquid originating from cell culture. Thus, in one embodiment, the present invention is a system for the purification of antibodies from a liquid, which system comprises a first chromatography column packed with a resin the ligands of which comprise Protein A or Protein G; a second chromatography column packed with a multi-modal chromatography resin comprising at least one cation-exchanging group and at least one aromatic or heteroaromatic ring system; means for adding sample and elution buffer to the first column; means for adding eluent originating from the first column to the second column; pumping means; and valving. The resins for the first and second chromatography columns may be as discussed above. In an advantageous embodiment, the system is automated. Such an automated system may be controlled by conventional tools for process control.

DETAILED DESCRIPTION OF THE DRAWINGS

In the chromatograms below (FIGS. 1-6, 7 and 9), the colour indications are as follows: Blue or red line (XX): $A_{280}$ nm; Green line (YY): fluorescence; Brown line (ZZ): conductivity (mS/cm); Grey line (OO): pH.

FIG. 1 shows the results of control experiment 1, as disclosed in Example 2(a) below. The injection of 2 ml MAb-Protein A mixture was via bypass, and 0.5 ml fractions were collected. It appears clearly from FIG. 1 how the relative magnitude of the $A_{280}$ curve and the fluorescence emission were in good agreement.

FIG. 2 shows the results of control experiment 2, as disclosed in Example 2(a) below. 2 ml of solution comprising fluorescence-labelled Protein A was injected into a column comprising the reference resin SP Sepharose™ Fast Flow (FF) (Amersham Biosciences). Gradient elution was used, and 1 ml fractions were collected. Again, a good agreement was observed between the $A_{280}$ curve and the fluorescence emission.

FIG. 3 shows the results of control experiment 3, as disclosed in Example 2(a) below. The Protein A-solution was injected to the multi-modal media prototype U790 P73, which is described in Example 2, Materials and Methods, below. Gradient elution was used, and 1 ml fractions were collected. Also in this case, a good agreement was observed between the $A_{280}$ curve and the fluorescence emission.

FIG. 4 shows the separation of MAb and MAb-Protein A aggregates in binding mode, as disclosed in example 2(b) below. Again, the multi-modal media prototype U790 P73 was used. A gradient of 0-100% B in 20 column volumes (CV) was used for elution. A-buffer (equilibration) was used at pH 5.0, and B-buffer as defined in Example 2, Materials and Methods, below.

FIG. 5 shows the separation of MAb and MAb-Protein A aggregates using further optimised conditions, as disclosed in example 2(b) below. The multi-modal media prototype U790 P73 was used. An optimised gradient of 0-77% B in 0 CV, 77% B for 30 CV, and 77-100% B CV was used. A-buffer (equilibration) was used at pH 4.5, B-buffer as defined in Example 2, Materials and Methods, below.

FIG. 6 shows the results of peak analysis by gel filtration on Superdex™ 200, as described in the Example 2 below. The peaks analysed are shown in FIG. 5. More specifically, FIG. 6A shows the results from gel filtration of fraction A9 (from the top of main UV-peak), while FIG. 6B shows the results from gel filtration fraction C7 (from the top of the fluorescence peak). In FIG. 6A, no MAb-Protein A aggregates were detectable. In FIG. 6B, MAb-Protein A aggregates were detectable by two peaks in the chromatogram before the MAb peak. This is a good indication that MAb-Protein A aggregates can be separated from MAbs using the multi-modal chromatography method according to the invention.

FIG. 7 shows the separation of pure MAb and MAb-Protein A aggregates in flow-through mode, as described in Example 2(c) below. The prototype multi-modal ligand U790 P73 was used. The sample volume was 6.5 ml (4.4 mg MAb/ml). The sample comprised MAb with addition of unlabeled (blue line) or with fluorescent labelled (red line) Protein A. 97% B=0.13 M NaCl (equilibration) was used. A-buffer and B-buffer were as described in Materials and Methods, below.

FIG. 8 shows the results of peak analysis by gel filtration on Superdex™ 200, as described Example 2. The peaks analysed are shown in FIG. 7. The sample volume was 100 µl, the flow rate was 0.5 ml/min, and the buffer was as described in Materials and Methods below. More specifically, FIG. 8A illustrates fraction A7, from run with non-labelled Protein A; top of the flow-through peak; FIG. 8B illustrates fraction B3, from run with non-labelled Protein A; top of eluted peak; and FIG. 8C illustrates fraction B3, from run with fluorescent labelled Protein A. The red curve shows UV, while the green plot shows fluorescence.

FIG. 9 shows the separation of pure MAb and MAb-Protein A aggregates in flow-through mode, as described below in Example 2(c). The prototype U790 P73 was used. The sample was substantially larger than what was used to obtain FIG. 7 above, namely 50 ml MAb 4.2 mg/ml (in total 210 mg MAb; with addition of fluorescent labelled Protein A). Experimental conditions: 97% B=0.13 M NaCl (equilibration). The A-buffer and B-buffer were as described above under Materials and Methods. Blue line: UV (280 nm), brown line: conductivity, green plot: fluorescence.

FIG. 10 shows the results of analysis of peaks presented in FIG. 9 obtained by gel filtration on Superdex™ 200, as described in the Example 2:

Flow-through fractions: A2, A5, A8, A11, A15, B3, B6, B9 and B11.

Eluted fraction: C2. The sample volume was 100 µl, while the flow rate was 0.5 ml/min. The buffer was as described in Materials and Methods, below. FIG. 10A shows an overlay of chromatograms from gel filtration of selected fractions from FIG. 9, while FIG. 10B shows a zoom of FIG. 10A. MAb-Protein A aggregates were detectable in the eluted peak, but not in the flow-through fractions. This result indicates that substantially all the MAb-Protein A aggregates adsorb to the column and are eluted again by an increase in conductivity.

EXPERIMENTAL PART

The present examples are provided for illustrative purposes only, and should not be interpreted in any way as limiting the scope of the invention as defined by the appended claims. All references provided below and elsewhere in the present specification are hereby included herein via reference.

Example 1

Multi-Modal Chromatography Resin

The volumes of matrix given below refer to settled bed volume. The weights of matrix given in gram refer to suction (water pump) dry weight. It is understood that these matrices are still water solvated material. The stirring referred to below was by a suspended, motor-driven stirrer, since the use of magnet bar stirrer is prompt to damage the beads. The analysis of the functionality and the determination of the degree of allylation, epoxidation, or the degree of substitution of ion exchanger groups on the beads refer to conventional methods which are well known to the skilled person in this field. The methods below were eventually complemented by additional elementary analysis of the gels in particular for sulphur atom.

TABLE 1

Chemical structures of ligand prototypes

| Ligand structure | Prototype no. |
|---|---|
| [structure: propylsulfonyl aminothiophene carboxylic acid] | U1012054 |
| [structure: homocysteine with benzamide] | U790P73 |
| [structure: homocysteine with 3,4,5-trimethoxybenzamide] | U790P65 |
| [structure: thioether with phenyl glutaric acid amide] | U790P71 |

Example 1(a)

Ligand Prototype U1012054

In this example, it is described how 3-amino-4(propylsulfonyl)thiophene-2-carboxylic acid was coupled to an NHS-activated agarose carrier.

Preparation of thiopropionic acid Sepharose: Bromine was added to a stirred suspension of 100 ml of allyl activated (0.3 mmol allyl/ml) Sepharose™ 6 Fast Flow gel (Amersham Biosciences), 4 g of AcONa and 100 ml of distilled water, till a persistent yellow colour was obtained. Sodium formate was then added till the suspension was fully decolourised. The reaction mixture was filtered and the gel washed with 500 ml of distilled water. The activated gel was then directly transfer to a reaction vessel and treated with an aqueous solution (50 ml dist. water) of 17.5 ml of thiopropionic acid (6 equivalents per allyl group) and 12 g of NaCl which pH was adjusted to 11.5 with 50% aq. NaOH before the addition. The reaction was left for 18 hours under stirring at 50° C. Filtration of the reaction mixture and washing with 500 ml of distilled water resulted in the thiopropionic Sepharose gel with a degree of substitution 0.29 mmol $CO_2H$ group/ml of gel.

Activation of gel with N-hydroxysuccinimide: 100 ml of the resulting thiopropionic acid Sepharose was then washed successively with 300 ml 1 M NaCl, 500 ml 0.1 M HCl, 500 ml 50% aq. acetone, 500 ml acetone. After the washings the gel was left to settle in acetone, the supernatant siphoned off and the settled beads transferred to a reaction vessel with help of 20 ml of acetone. A solution of 15.2 g of N-hydroxysuccinimide (NHS) in 80 ml of acetone and another solution of dicyclohexylcarbodiimide in 80 ml of acetone were then both added. The reaction slurry was left under stirring at 30° C. for 18 hours. After filtration, the gel was slowly washed (gravity flow) with 10 times 150 ml isopropanol over a full working day. The degree of NHS-activation was estimated after reaction with $NH_4OH$ to be about 80%, corresponding to an activation of about 0.23 mmol of NHS function/ml of gel.

Coupling of ligand to NHS-activated thiopropionic acid Sepharose: 3-amino-4(propylsulfonyl)thiophene-2-carboxylic acid was prepared as described in WO 02/05959 (ligand 12). A soluble mixture of a solution of 565 mg of 3-amino-4(propylsulfonyl)thiophene-2-carboxylic acid (2.27 mmol) in 2 ml of dist. water, 2 ml of 1M $NaHCO_3$ and 2 ml of ethanol was prepared and adjusted to pH 8.5 with careful addition of 50% aqueous NaOH.

NHS-activated thiopropionic acid Sepharose (10 ml) was quickly washed with 20 ml ice cold 1 mM HCl solution. The gel was then transferred to an Erlenmeyer to which the thineyl serine solution was added. The reaction mixture was left on a shaking table (150 rpm) at room temperature for 18 hours.

After filtration of the reaction mixture, the gel was washed successively, with 40 ml distilled water, 20 ml ethanol, 20 ml 0.25 M aq. ethanolamine, 20 ml distilled water, 20 ml 1M aq. NaCl, and 20 ml of distilled water.

Examples 1 (b)-(d)

In examples 1(b)-(d) below, the prototype ligands U790P65, U790P71 and U790P73 were prepared using D,L-homocysteine thiolactone as a scaffold, as described in WO 03/024588. In brief, after formation of the amide bound by reacting homocysteine thiolactone with acyl chlorides or anhydrides, the opening of the thiolactone ring was realised with basic hydrolysis and the resulting compound further coupled to an activated Sepharose™ 6FF (Amersham Biosciences).

Example 1(b)

Ligand Prototype U790P73

A solution of benzoyl chloride (8.7 ml, 75 mmol) in 30 ml DCM was added drop wise to a solution of D,L-homocysteine thiolactone (11.5 g, 75 mmol) and di-isopropylamine (DIPEA) (26 ml, 150 mmol) in dichloromethane (DCM, 120 ml) at 0° C. The mixture was stirred overnight at room temperature. The solvent was evaporated under vacuum and the reaction residue was extracted with ethyl acetate (300 ml). The organic phase was washed with aq. citric acid 10% (w/w, 200 ml), aq. $K_2CO_3$ 10% (200 ml), water (200 ml), and dried with sodium sulphate. After filtration, the solvent was removed yielding a white solid (13.8 g, 83%). At 0° C., a 5N- sodium hydroxide solution (5 ml) was added to 276 mg (1.25 mmol) of the white solid and the mixture was further stirred for 2 hours at room temperature. Brominated Sepharose™ 6 Fast Flow (10 ml) (Amersham Biosciences), obtained following a well known procedure starting from an allylated Sepharose™ 6 Fast Flow (250 µmol/ml), was mixed with the alkaline solution of the ligand (described above) and warmed up to 50° C. overnight. After reaction, the gel was filtered and washed with water (2×150 ml), ethanol (2×150 ml), acetic acid 0.2M (2×150 ml) and water (2×150 ml). The ionic capacity of the gel was then measured by titration of the acid groups and gave 103 µmol/ml of gel.

Example 1 (c)

Ligand Prototype U790P65

A solution of 3,4,5-trimethoxy-benzoyl chloride (2.37 g, 10.3 mmol) in 4 ml DCM was added drop wise to a solution of D,L-homocysteine thiolactone (1.58 g, 10.3 mmol) and di-isopropylamine (DIPEA) (3.58 ml, 20.6 mmol) in dichloromethane (DCM, 6 ml) at 0° C. The mixture was stirred overnight at room temperature. The solvent was evaporated under vacuum and the reaction residue was extracted with ethyl acetate (50 ml). The organic phase was washed with aq. citric acid 10% (w/w, 30 ml), aq. K$_2$CO$_3$ 10% (30 ml), water (30 ml), and dried with sodium sulphate. After filtration, the solvent was removed yielding a white solid (2.21 g, 69%). At 0° C., a 5N sodium hydroxide solution (5 ml) was added to 389 mg (1.25 mmol) of the white solid and the mixture was further stirred for 2 hours at room temperature. Brominated Sepharose™ 6 Fast Flow (10 ml) (Amersham Biosciences), obtained following a well known procedure starting from an allylated Sepharose™ 6 fast Flow (250 µmol/ml), was mixed with the alkaline solution of the ligand (described above) and warmed up to 50° C. overnight. After reaction, the gel was filtered and washed with water (2×150 ml), ethanol (2×150 ml), acetic acid 0.2M (2×150 ml) and water (2×150 ml). The ionic capacity of the gel was then measured to be 59 µmol/ml of gel.

Example 1 (d)

Ligand Prototype U790P71

A solution of phenyl glutaric anhydride (1.96 g, 10.3 mmol) in 4 ml DCM was added drop wise to a solution of D,L-homocysteine thiolactone (1.58 g, 10.3 mmol) and diisopropylamine (DIPEA) (3.58 ml, 20.6 mmol) in dichloromethane (DCM, 6 ml) at 0° C. The mixture was stirred overnight at room temperature. The solvent was evaporated under vacuum and the reaction residue was directly treated with a 5N sodium hydroxide solution (10 ml) and further stirred for 2 hours at room temperature. Brominated Sepharose™ 6 Fast Flow (10 ml) (Amersham Biosciences), obtained following a well known procedure starting from an allylated Sepharose™ 6 Fast Flow (250 µmol/ml), was mixed with 1.4 ml of the alkaline solution of the ligand described above and warmed up to 50° C. overnight. After reaction, the gel was filtered and washed with water (2×150 ml), ethanol (2×150 ml), acetic acid 0.2M (2×150 ml) and water (2×150 ml). The ionic capacity of the gels was then measured to be 110 µmol/ml of gel corresponding to a ligand substitution level of 55 µmol/ml of gel.

Example 2

Separation of Antibodies

Materials

| | |
|---|---|
| Chromatography system | ÄKTA ™ Explorer 100 with UNICORN v. 4.0 software (Amersham Biosciences) |
| Spectrophotometer | Ultrospec ™ 3000pro (Amersham Biosciences) |
| Fluorescence spectrometer | SPEX Fluorolog-3 from JY Horiba (Edison, NJ, USA) |
| Acetic acid | Merck cat. no. 1.00063, p.a. (Pro Analysi) |
| Na-succinate | BDH, cat. No. 30219 |
| NaCl | Merck cat. no. 1.06404, p.a. |
| Tris | Merck cat. no. 1.08382, p.a. |
| NaOH | Merck cat. no. 1.06469, p.a. |
| MES | SIGMA cat no. M3671 |
| Na$_2$CO$_3$ | Merck cat no. 1.06392.1000, p.a. |
| Water | MilliQ-water was used |
| Cy 5 reactive dye | Amersham Biosciences |
| SP Sepharose ™ Fast Flow (control) | Amersham Biosciences |
| Superdex ™ 200 10/300 (gel filtration) | Amersham Biosciences |

For separation of pure MAb and MAb-Protein A aggregates under binding conditions, the following buffers were used:

A-buffer (equilibration): 100 mM acetic acid, 20 mM Na-succinate pH 4.5-5.0

B-buffer: 100 mM acetic acid, 20 mM Na-succinate, 1.5 M NaCl pH 6.4

For separation of pure MAb and MAb-Protein A aggregates in flow-through mode, the following buffers were used:

A-buffer: 50 mM MES, 1 M NaCl pH 7

B-buffer: 50 mM MES 0.1 M NaCl pH 7.0

For gel filtration on, the following conditions were used:

50 mM Phosphate buffer, 0.150 M NaCl, pH 7.0

Monoclonal humanised IgG1 antibodies, pI 9, (Genentech) was submitted to an initial purification on Protein A media (MabSelect, Amersham Biosciences).

Native Protein A was obtained from Novozymes (Batch NDP 1023).

Methods

Column packing and test: Gel slurry was poured in HR5/5 columns partially filled with Milli Q water. A top adaptor was lowered towards the gel surface without compression of the gel. The gel was then packed at 1.2 ml/min until the bed was stable. The adaptor was then lowered to touch the gel surface. Packing performance (i.e. plate number and asymmetry) was evaluated by injection of 25 µl 2% acetone.

Fluorescence labelling of Protein A: 200 µl Protein A solution (~50 mg/ml) was diluted with 1000 µl 0.1 M Na$_2$CO$_3$ pH 9.3.

The solution was transferred to a vial of Cy5 reactive dye. Incubation at room temperature for 30 minutes, followed by desalting on a PD10 column, equilibrated with 100 mM HAc, 20 mM Na-succinate pH 5.0. The labelled Protein A was then diluted 1:5 with unlabelled Protein A to a final concentration of ~41 mg/ml.

Sample preparation: Three replicates of the MAb-samples were measured in a spectrophotometer at 280 nm. The average value of the absorbance was used for concentration determination. The MAb concentration was determined to 4.4 mg/ml according to $$C=A/(l\times\epsilon)$$

wherein:
C=concentration of IgG
A=absorbance at 280 nm
l=path length
$\epsilon$=molar extinction coefficient for the MAb, mg ml$^{-1}$=1.46.

Fluorescent labelled Protein A solution was added to the MAb sample in the proportions 1:1000 (w/w).

In flow-through mode, the ionic strength was adjusted by addition of NaCl (for details, see below).

Fluorescence measurements for detection of Protein A: Measurement of relative Protein A concentration in collected fractions was performed by use of a fluorescence spectrometer (SPEX Fluorolog-3). Excitation of Cy5 was performed at 630 nm, and detection of the fluorescence emission at 670 nm.

Gel filtration: To test for MAb-Protein A aggregation gel filtration was performed using a pre-packed column packed with Superdex™ 200 (Amersham Biosciences). Selected fractions from the prototype runs were analysed. The sample volume was 100 µl and the flow rate was 0.5 ml/min.

Equilibration: 2 column volumes (CV) Buffer (first-time use).

Equilibration: 0.1 CV Buffer (Between runs).

Sample injection: 100 µl. Isocratic elution: 1.2 CV buffer.

Analysis of Protein A concentration: The samples were diluted (with sample diluent for the Protein A assay) in the proportions 200 µl sample+800 µl diluent. After mixing, the test tubes were boiled in a water bath for 10 minutes, and then mixed again. The samples were then subjected to analysis of Protein A content.

Example 2(a)

Control Experiments Under Binding Conditions

Fluorescent labelled Protein A was mixed with MAb solution as described above. To ensure that the fluorescent labelling did not affect the chromatographic properties of Protein A, and to set a correct delay value in ÄKTA™ Explorer (Amersham Biosciences), three different control experiments were performed as follows:

Control experiment 1: Injection of MAb-Protein A mixture via bypass and collection of 0.5 ml fractions. Comparison of absorbance curve and fluorescence in collected fractions. As shown in FIG. 1, after correct setting of the system delay volume, the relative magnitudes of the $A_{280}$ curve and fluorescence emission were in good agreement.

Control experiment 2: Injection of 2 ml Protein A solution to SP Sepharose™ Fast Flow. Gradient elution and fraction collection (1 ml/fraction). Elution of Protein A was monitored by absorbance at 280 nm and by measurement of fluorescence in the collected fractions. Also in this case a good agreement could be observed between the $A_{280}$ curve and fluorescence emission, see FIG. 2.

Control experiment 3: As control 2, but injection of Protein A-solution to media prototype U790 P73 (see example 1 (b) above). Also with the multi-modal media prototype, good agreement could be observed between the $A_{280}$ curve and fluorescence emission (FIG. 3), and no separation was obtained between non-labelled and labelled Protein A.

Example 2(b)

Separation of MAb and MAb-Protein A Aggregates in Binding Mode 2 ml MAb-Protein A mixture was injected to the different media prototypes. Gradient elution and fraction collection as above. Elution of MAb and MAb-Protein A aggregates was followed by monitoring the absorbance at 280 nm, and the elution conductivity and also by measurement of fluorescence in the collected fractions. The difference in retention volume between the absorbance curve and fluorescence emission was calculated for each prototype. The results are shown in table 2 and FIG. 4. Even though the number of data points are low, and the variation relatively high, it can be concluded that higher elution conductivity results in better separation between the UV- and fluorescence peaks (i.e. between MAb and MAb-Protein A aggregates). No separation was obtained on the reference matrix SP Sepharose™ Fast Flow.

TABLE 2

Difference in retention volume (dRt) and elution conductivity between the absorbance curve and fluorescence emission

| Media | dRt (ml) | mS/cm |
| --- | --- | --- |
| SP Seph FF | 0 | 19.9 |
| U2054 | 1 | 38.5 |
| U790P65 | 1.6 | 50.4 |
| U790P71 | 0.5 | 45.6 |
| U790P73 | 3.5 | 84.2 |

The separation obtained on prototype U790 P73 was further optimised by adjusting pH of the sample, which had minor effect on the separation, and optimisation of the gradient. In one experiment (results not shown), dRt was increased to 6 ml by use of a shallower gradient, namely 40 CV instead of 20. A much better separation was obtained by step elution (FIG. 5). In this way part of the fluorescence could be completely separated from the main peak. Different fractions in the chromatogram were analysed by gel filtration on Superdex™ 200 (FIG. 6). MAb-Protein A aggregates could be detected in the fluorescence peak, i.e. two peaks in the chromatogram before the MAb peak, but not in the main UV-peak. This result indicates that it is possible to separate MAb-Protein A aggregates from MAb by use of multi-modal ligands.

Example 2(c)

Separation of MAb and MAb-Protein A Aggregates in Flow-Through Mode

Two experiments were performed in flow-through mode using addition of unlabeled and fluorescent labelled Protein A (conditions: 97% B=0.13 M NaCl). The results revealed that the chromatograms were almost identical (FIG. 7). As above, different fractions were analysed by gel filtration on Superdex™ 200 (FIG. 8A-B). MAb-Protein A aggregates could be detected in the eluted peak, but not in the flow-through. Furthermore, fluorescence emission in the Superdex™ fractions could be detected in the two minor peaks in the chromatogram, but not in the main MAb-peak (FIG. 8C). Thus, these results show that it is possible to separate MAb-Protein A aggregates from MAb in flow-through mode. Thus, most the Protein A-antibody aggregates adsorbed, while approximately 95% of the MAbs passed directly through the column.

To further investigate the potential of the method for separation of MAb and MAb-Protein A aggregates in flow-through mode, 50 ml of MAb-Protein A mixture (in total 210 mg MAb) was applied on the 1 ml column (FIG. 9). 98.4% of the protein passed directly through the column (based on mAU*ml), and a small peak (1.6%) was eluted by increasing the conductivity. The fractions were analysed by gel filtration on Superdex™ 200 and by detection of fluorescence emission. Furthermore, samples were prepared for Protein A analysis as described above.

Results from gel filtration are shown in FIG. 10. As above, MAb-Protein A aggregates could be detected in the eluted peak, but not in the flow-through fractions. This result indicates that most of the MAb-Protein A aggregates adsorbs to the column and is eluted again by an increase in conductivity.

Fluorescence measurements show that the fluorescence emission, i.e. the Protein A content, gradually increased in flow-through during sample application. However 90% of the fluorescence was found in the eluted peak. This observation was confirmed by analysis of protein A concentration (table 3). Thus, approximately 99% of the MAb-Protein A aggregates were removed when 40 mg MAb/ml adsorbent had been applied, and 96% at the highest sample load (210 mg/ml).

TABLE 3

Results from analysis of Protein A concentration in flow-through and eluate peaks

| Sample | Applied amount (mg/ml adsorbent) | ng SPA/ml | Protein A conc (%) |
|---|---|---|---|
| Start material | — | 1199 | — |
| Fraction A5 | 42 | 14.6 | 1.2 |
| Fraction A11 | 92.4 | 53.5 | 4.5 |
| Fraction B9 | 201.6 | 146 | 12.2 |
| Pool fraction A1-A14 | 117.6 | 15.8 | 1.3 |
| Pool fraction A1-B12 | 210 | 48.7 | 4.1 |
| Pool fraction A15-B12 | 126 to 210 | 84.3 | 7 |
| Fraction C2 (eluted fraction) | 210 | 10450 | 872 |

The invention claimed is:

1. A method of separating antibodies from one or more contaminants in a solution, comprising contacting the solution, which is an antibody-containing eluate from an affinity chromatography resin, with a second chromatography resin comprised of a support to which multi-modal ligands have been immobilised, wherein a multi-modal ligand comprises at least one cation-exchanging group and at least one aromatic or heteroaromatic ring system, to adsorb antibodies and/or contaminants to the resin.

2. The method of claim 1, wherein the ring-forming atoms of the hereoaromatic ring system are selected from the group consisting of C, S or O.

3. The method of claim 1, wherein the cation-exchanging group is a weak cation exchanger.

4. The method of claim 1, wherein the contaminants comprise complexes formed between released affinity ligands and antibodies, and/or aggregates of released affinity ligands and/or antibodies.

5. The method of claim 1, wherein the contaminants are adsorbed to the second chromatography resin.

6. The method of claim 1, further comprising eluting antibodies and/or contaminants from the second chromatography resin.

7. The method of claim 1, wherein the antibodies are monoclonal antibodies.

8. The method of claim 1, wherein the solution is an antibody-containing eluate from an affinity chromatography resin the ligands of which comprise Protein A.

* * * * *